(12) United States Patent
Hepford

(10) Patent No.: US 12,239,690 B1
(45) Date of Patent: Mar. 4, 2025

(54) METHOD AND SYSTEM FOR TUNING HORMONE RECEPTORS THROUGH THE DYNAMIC INTRAVENOUS DELIVERY OF A HORMONE ACCORDING TO A TARGET PHYSIOLOGICAL CADENCE

(71) Applicant: WELL CELL GLOBAL LLC, Houston, TX (US)

(72) Inventor: Scott A Hepford, Houston, TX (US)

(73) Assignee: WELL CELL GLOBAL LLC, Houston, TX (US)

(*) Notice: Subject to any disclaimer, the term of this patent is extended or adjusted under 35 U.S.C. 154(b) by 0 days.

(21) Appl. No.: 18/735,124

(22) Filed: Jun. 5, 2024

(51) Int. Cl.
  *A61K 38/22* (2006.01)
  *A61K 31/565* (2006.01)
  *A61M 5/172* (2006.01)
  *G16H 20/17* (2018.01)

(52) U.S. Cl.
  CPC ........ *A61K 38/2257* (2013.01); *A61K 31/565* (2013.01); *A61K 38/22* (2013.01); *A61M 5/1723* (2013.01); *G16H 20/17* (2018.01); *A61M 2202/04* (2013.01); *A61M 2205/3303* (2013.01)

(58) Field of Classification Search
  None
  See application file for complete search history.

(56) References Cited

U.S. PATENT DOCUMENTS

| | | |
|---|---|---|
| 9,652,595 B1 | 5/2017 | Carr et al. |
| 10,533,990 B2 | 1/2020 | Carr et al. |
| 2014/0005633 A1 | 1/2014 | Finan |
| 2019/0086394 A1 | 3/2019 | Carr et al. |
| 2022/0383991 A1* | 12/2022 | Mould ........... G16H 50/20 |

OTHER PUBLICATIONS

Rebello, C.J., et al.; Physiologic hormone administration improves HbA1C in Native Americans with type 2 diabetes: A retrospective study and review of insulin secretion and action; Obesity Reviews; Wiley Online Library; Aug. 14, 2023; pp. 1-12; vol. 24, Issue 12; <https://doi.org/10.1111/obr.13625>.

(Continued)

*Primary Examiner* — Manuel A Mendez
(74) *Attorney, Agent, or Firm* — Kearney, McWilliams & Davis; Erik J. Osterrieder

(57) ABSTRACT

A system and method for tuning hormone receptors through the dynamic intravenous introduction of a hormone in a manner that mimics a target physiological secretion cadence of that hormone is presented herein. In particular, a dosing model is developed with a desired goal of creating a hormone delivery plan with a dosing waveform that resembles a waveform associated with the target physiological secretion cadence of the hormone. Several bolus delivery specifications, including volume, frequency and pressure, are dynamically defined such that, over a specified period of time, the bolus introductions create the desired dosing waveform. The dosing model is then executed through a plurality of successive and dynamic intravenous exogenous bolus introductions of the hormone according to the plurality of bolus delivery specifications.

20 Claims, 8 Drawing Sheets

(56) References Cited

OTHER PUBLICATIONS

Greenway, F., et al.; Physiologic Insulin Resensitization as a Treatment Modality for Insulin Resistance Pathophysiology. International Journal of Molecular Sciences; Feb. 8, 2022; pp. 1-12; 23(3):1884; <https://doi.org/10.3390/ijms23031884>.

Lewis, S.T.,et al .; A Receptor Story: Insulin Resistance Pathophysiology and Physiologic Insulin Resensitization's Role as a Treatment Modality. International Journal of Molecular Sciences; Jun. 30, 2023; pp. 1-11; 24(13):10927; <https://doi.org/10.3390/ijms241310927>.

Loveridge, B, et al.; Improved HOMA-IR Insulin Sensitivity and Glycemic Control Utilizing Physiologic Insulin Resensitization. Archives of Clinical and Medical Case Reports. Fortune Journals, vol. 7, Issue 6, Dec. 26, 2023: 439-444; DOI:10.26502/acmcr.96550644.

Bissada, J.E., et al.; Adjunctive Care in Sequential Diabetic Foot Wounds: Case Study; American Journal Biomedical Science & Research; Apr. 10, 2024; vol. 22(1); pp. 62-67; DOI: 10.34297/AJBSR.2024.21.002916.

Villaverde, Z. et al.; Improved Kidney Function Following Physiologic Insulin Resensitization Treatment Modality; Journal of Endocrinology and Disorders; Auctores Publishing; Jul. 30, 2021; vol. 5(4); pp. 1-4; <https://doi.org/10.31579/2640-1045/080>.

Tucker, T., et al.; Case Series: Reversal of Diabetic Neuropathy Utilizing Physiologic Insulin Resensitization; International Journal of Diabetes & Metabolic Disorders; Jul. 20, 2021; vol. 6, Issue 2; pp. 160-163.

Pham, R.T., et al.; Reversal of diabetic retinopathy in two patients following theuse of physiologic insulin Resensitization; Journal of Diabetes and Its Complications; Elsevier; Jun. 25, 2023; vol. 37; 108549; pp. 1-4; <https://doi.org/10.1016/j.jdiacomp.2023.108549>.

Loveridge, B., et al.; Dynamic diabetes solutions: physiologic insulin resensitization; Medical & Clinical Research; Aug. 13, 2021; vol. 6; Issue 8; pp. 656-660.

Greenway, F, et al.; Efficacy of Physiologic Insulin Resensitization as a Treatment for Insulin Resistance Pathophysiology; Recent Updates in Disease and Health Research vol. 6, May 9, 2024, pp. 1-19. https://doi.org/10.9734/bpi/rudhr/v6/3199G.

Yang, J-H., et al,; Chemically induced reprogramming to reverse cellular aging; Aging 2023; vol. 15, No. 13, www.aging-us.com; Jul. 12, 2023; pp. 5966-5989.

\* cited by examiner

FIG. 7

METHOD AND SYSTEM FOR TUNING HORMONE RECEPTORS THROUGH THE DYNAMIC INTRAVENOUS DELIVERY OF A HORMONE ACCORDING TO A TARGET PHYSIOLOGICAL CADENCE

FIELD OF THE INVENTION

The present invention is generally directed to a system and method for restoring and/or tuning hormone receptors in a human body, and more specifically, a system and method for tuning hormone receptors through the precise, controlled and in some cases, dynamic intravenous delivery of at least one hormone according to a target physiological cadence of that hormone.

BACKGROUND OF THE INVENTION

In the human body, rather than a continuous flow or stream, several, if not all hormones are released or secreted in periodic waves or an oscillating or pulsatile pattern, often followed by distinct trough periods that stimulate ligand and receptor activation. In some cases, the periodic waves dynamically change based upon the body's demands. Many, but not all, of such hormones are physiologically designed to have receptors on the surface of effector cells that bind to their respective ligand or hormone. In some cases, the hormone and/or ligand is brought into the cell where it separates from the receptor, and the receptor then migrates back to the cell's surface, ready to bind with another hormone or ligand molecule.

In any case, the cyclical, oscillating and/or pulsatile secretion of such hormones in the human body by various organs or glands plays a crucial role in the overall maintenance of homeostasis and the regulation of various physiological processes in the human body. In other words, the disruption of the oscillating or pulsatile secretion of a hormone can disrupt or affect homeostasis, and depending on the particular hormone and several other factors associated with the particular subject, can cause several mild to severe disturbances or disorders in the body, sometimes leading to permanent tissue or organ damage or failure.

In particular, the disruption of the oscillating or pulsatile secretion of a hormone can occur as a result of several various instances, some known and some unknown. For example, over-stimulation or over-exposure of a particular hormone can, over time, cause the particular hormone receptor to become less responsive to the hormone or downregulate. This often occurs in patients with Type 2 diabetes who are exposed to high levels of insulin, often causing a condition commonly known as hyperinsulinemia due to the concentration of insulin in the blood remaining higher than normal for prolonged periods of time.

However, disruption of the oscillating or pulsatile secretion of a hormone is in no way limited to diabetic conditions or diabetic patients, and can occur with virtually any hormone in the human body, including, for example, but in no way limited to insulin, oxytocin, prolactin, estrogen, etc.

Furthermore, over-stimulation or over-exposure of a hormone is just one way in which the pulsatile secretion of a hormone can be disrupted and/or in which the corresponding hormone receptor(s) can be disturbed. Other cases can include, but are in no way limited to, genetic factors, environmental factors, the subject's diet or eating habits, lack of exercise, too much exercise, etc. It is also worth noting that, in some cases, the cause of the disruption to the hormone receptor and/or pulsatile secretion of a hormone may be unknown.

Moreover, in the human body, the physiological release or secretion of many hormones oscillates according to a regular or semi-regular period or time, and according to a particular or predictable pattern and/or a circadian rhythm modulated by the pineal gland. Those patterns of the physiological release of a hormone can be represented through a waveform in which the wavelength (e.g., measured between adjacent troughs) represents the period of release or secretion of the hormone. As just an example, insulin is released every four to eight minutes (4-8 min), and in some cases, every five to six minutes (5-6 min), resulting in a waveform with a wavelength that is completed in approximately 4-8 minutes.

Additionally, the frequency, amplitude and oscillating pattern of the physiological release of each hormone in the human body may be different from one another, resulting in several different waveforms that are representative of the particular oscillating pattern of the particular hormone. Depending on the particular hormone, those waveform patterns may include gradually curved crests and troughs (e.g., similar to a sine wave), sharp or narrow crests and troughs (e.g., similar to a spike wave), angular crests and troughs (e.g., similar to a square wave), etc.

Accordingly, there is a need in the art for a system and method for restoring the physiologic cadence of a hormone and for tuning hormone receptors in the human body. In some embodiments, this is accomplished through the precise and controlled intravenous delivery of at least one hormone according to a target physiological cadence of that hormone.

SUMMARY OF THE INVENTION

The present invention is generally directed to a method for tuning hormone receptors in a subject through the dynamic intravenous introduction of the hormone in a manner that mimics or closely resembles the natural or targeted physiological cadence of that hormone.

In particular, the method of at least one embodiment includes the step of determining the target physiologic cadence of the hormone. This can be accomplished by referencing one or more various materials, such as charts, look-up tables, books, research papers, publications, etc. that identify or define a known pulsatility of one or more particular hormones. The reference material(s) may, in some cases, include separate entries or itemized records for different demographics or classes of individuals, and are based on known information as a result of extensive research, testing, peer reviews, etc.

Next, with the hormone identified and the target physiological cadence of that hormone determined, a dosing model or treatment plan is then developed. The dosing model of the various embodiments is at least partially based on the target physiologic secretion cadence of the hormone, in that the desired goal is to create a hormone delivery plan or dosing model that will mimic or closely resemble the target physiological secretion cadence of the particular hormone, for example, insulin (or other hormone) naturally produced by the pancreas (or other organ or component of the human body.)

In this manner, the dosing model of at least one embodiment can also include one or more specific values or amounts for one or more bolus delivery specifications. Particularly, the bolus delivery specification(s), as used herein, can include, for example, a volume or an amount of the hormone or hormone solution to be delivered in a single bolus, a frequency or rate of several bolus introductions over a specified period of time, and an amount of pressure used to deliver each bolus introduction to the subject. Other bolus delivery specifications of other embodiments can include a type, size or gauge of the intravenous needle or delivery equipment, etc.

More specifically, the method of at least one embodiment includes a step of selecting or defining one or more of the bolus delivery specifications or parameters that will generate a bolus delivery waveform that at least partially resembles the target physiologic secretion cadence of the hormone. Again, the goal of at least one embodiment is to create a series of bolus introductions of the hormone or hormone solution that mimics or closely resembles the waveform pattern of the target physiologic secretion cadence.

As described herein, the specifications or parameters (e.g., frequency, volume, and pressure) from which the hormone is delivered to the subject can have a profound impact on the overall waveform pattern associated with the introduction of the hormone into the body.

In some cases or implementations of the present invention, one or more of the bolus delivery specifications or parameters (e.g., frequency, volume, pressure) are dynamic in that, based on the defined values in the dosing model, they can change within a single wavelength or otherwise within a predefined amount of time.

Finally, with the dosing model created and the dynamic delivery specifications or parameters defined, the method includes the step of executing the dosing model through a plurality of monitored, successive and dynamic intravenous exogenous bolus introductions of the hormone according to the plurality of bolus delivery specifications. Frequently, the subject's physiologic response to the dosing model, or a portion of the dosing model, is observed or examined (e.g., through one or more medical or clinical examinations, tests, or observations). If warranted, the dosing model can be altered for subsequent bolus introductions.

BRIEF DESCRIPTION OF DRAWINGS

FIG. 7 is an exemplary infusion flow sheet used in connection with at least one embodiment of the system and method disclosed herein.

Like reference numerals refer to like parts throughout the several views of the drawings provided herein.

DETAILED DESCRIPTION OF THE INVENTION

Figure 1A:
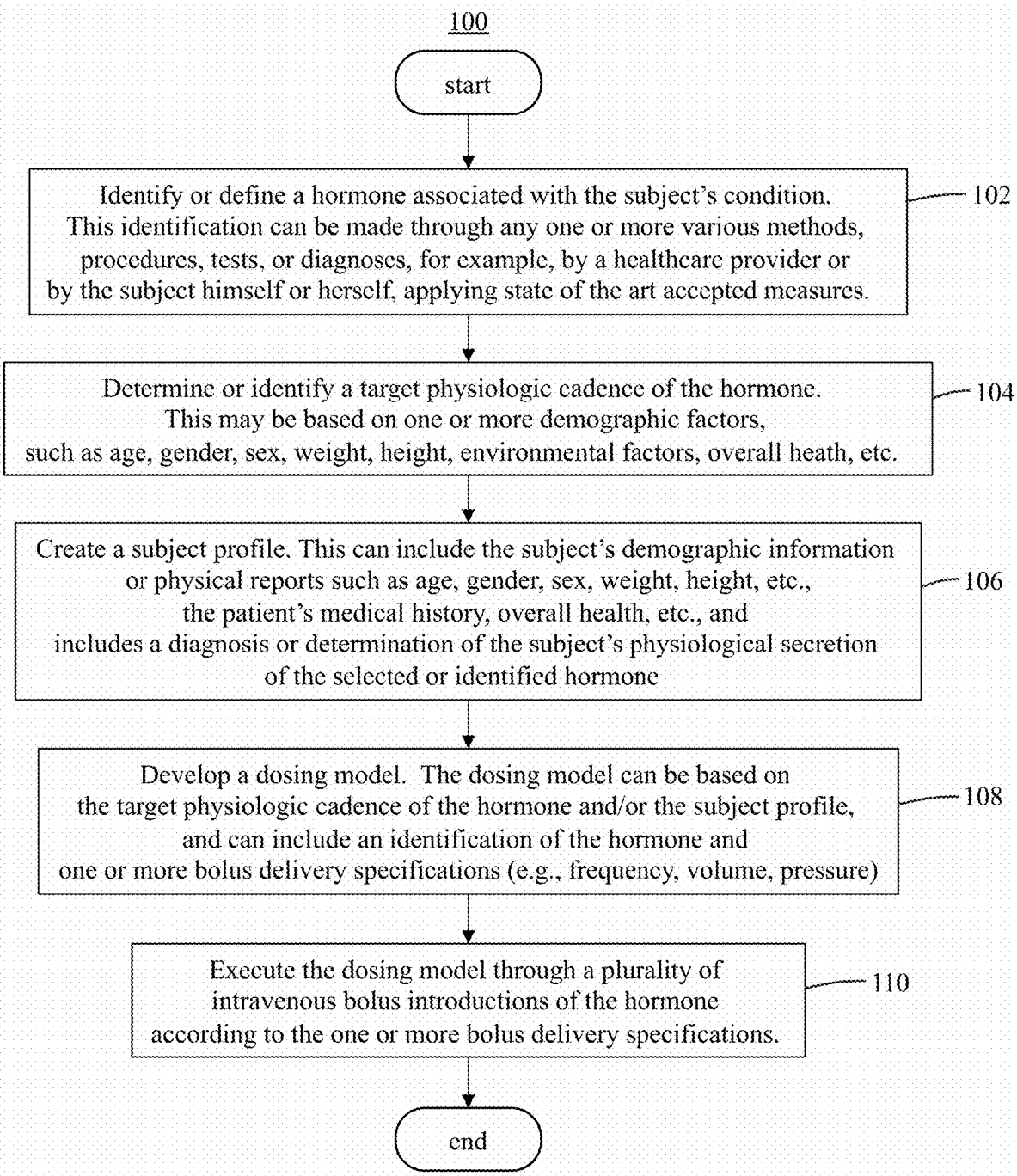
FIG. 1A is a high-level flow chart of the method for tuning hormone receptors through the dynamic intravenous delivery of at least one hormone according to a target physiological cadence of that hormone, as described in accordance with at least one embodiment of the present invention.
Figure 1B:
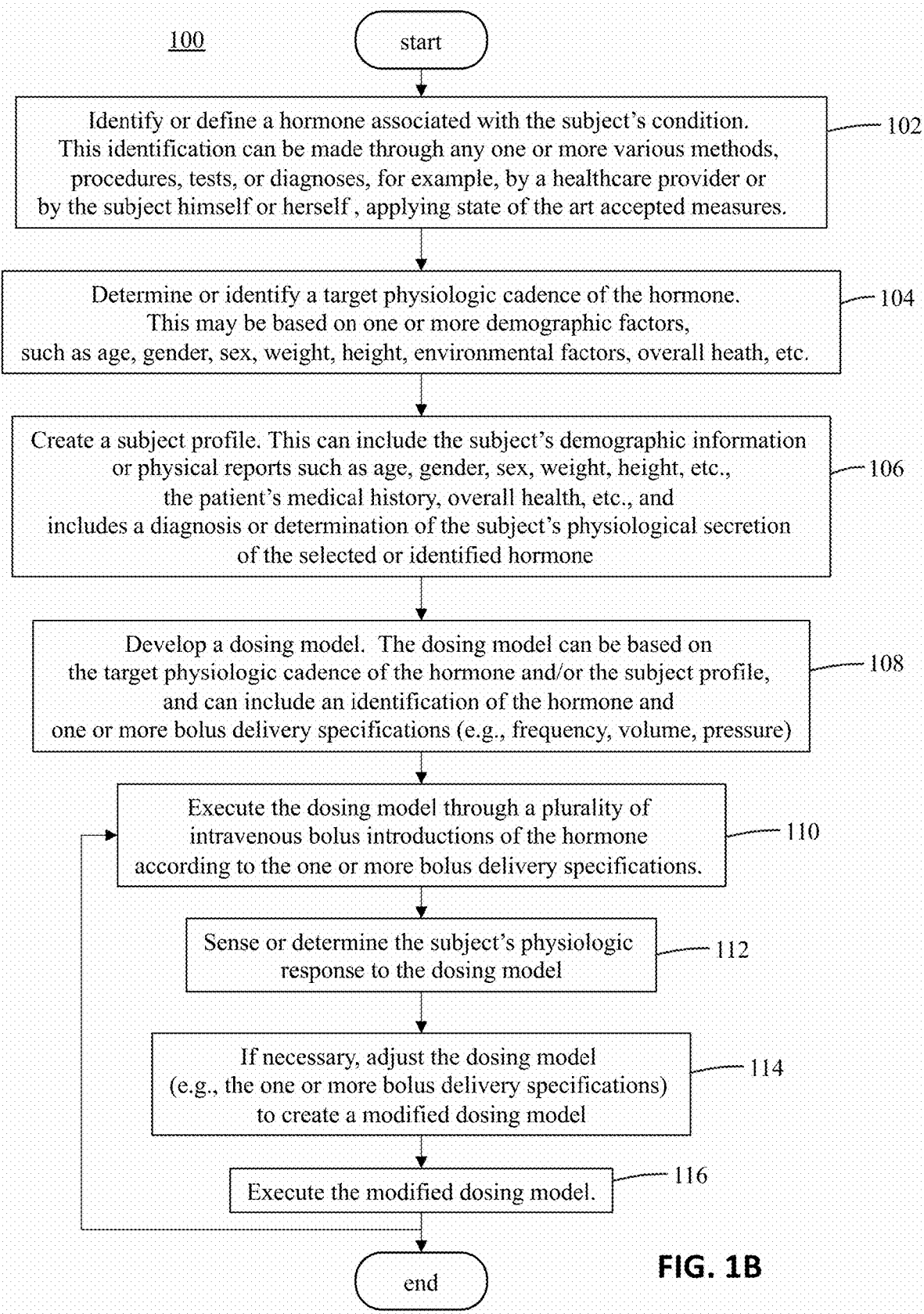
FIG. 1B is another high-level flow chart of the method for tuning hormone receptors through the dynamic intravenous delivery of at least one hormone according to a target physiological cadence of that hormone, as described in accordance with at least one embodiment of the present invention.

As shown in the accompanying drawings, and with particular reference to FIGS. 1A and 1B, for example, the present invention is generally directed to a system and method 100 for tuning one or more hormone receptors in the human body through the precise, controlled, and in some cases, dynamic intravenous delivery of at least one hormone according to a target physiological cadence of that hormone.

More specifically, as referenced at 102 in FIG. 1A, the method 100 of at least one embodiment includes, and in some cases, begins with an identification of the particular hormone to which the hormone receptors will bind. This identification can be made through any one or more various methods, procedures, tests, or diagnoses, for example, by a healthcare provider or by the subject himself or herself.

For instance, in the example provided above with regard to Type 1 or Type 2 diabetes, the subject may be experiencing hyperinsulinemia due to the concentration of insulin in the blood remaining higher than normal for prolonged periods. This can be diagnosed through any one or more tests, exams, or procedures such as a blood test that measures the subject's blood glucose levels, insulin levels, etc. In this example, the identified hormone is insulin; however, with other hormones, the identification process or procedure may be different.

More particularly, in other embodiments or implementations of the method 100 described herein, the identified hormone may be oxytocin, prolactin or estrogen due to a woman's infertility or inability to conceive. For example, the pituitary gland can cause excess production of prolactin, a condition commonly referred to a hyperprolactinemia, which can reduce estrogen production and cause infertility. In this case, the identified hormone for purposes of the method 100 described in accordance with at least one embodiment herein may be prolactin, oxytocin and/or estrogen. The identification of such a hormone, as represented at 102, may be through one or more blood tests (e.g., similar to the previous example with regard to hyperinsulinemia); however, for purposes of the method 100, the hormone may be identified by the healthcare provider (e.g., physician, endocrinologist, nurse, etc.) through observation and/or a series of questions/answers with the subject. In other words, physical tests and/or medical or clinical examinations may or may not play a role in the identification of the hormone 102 for the method 100 of various embodiments described herein.

As yet another example, a subject or patient, such as a child, adolescent or young adult, may be experiencing early-onset or late-onset of puberty for which treatment is sought. In those examples, the physician or healthcare provider may not need to perform any physical tests or medical exams to diagnose the subject with early-onset or late-onset of puberty. Rather, observation alone may be used to identify the condition (in this example, early-onset or late-onset of puberty) and the hormone(s) 102 for which the method 100 applies (e.g., in this example, gonadotropins).

Next, with the hormone(s) identified, as shown at 104 in FIG. 1A, the method 100 of at least one embodiment includes determining or identifying a target physiologic cadence or a target waveform pattern P of that hormone.

More specifically, as described above, in the human body, several hormones are released or secreted in an oscillating pattern, often followed by distinct trough periods that stimulate ligand and receptor activation. The physiological release or secretion of each hormone oscillates according to a particular period or time T, and according to a particular oscillating pattern P. The pattern P can be represented through a waveform in which the wavelength (e.g., measured between adjacent troughs) represents the period of release or secretion of the hormone.

Additionally, the frequency, amplitude, and oscillating pattern of the physiological release of each hormone in the human body may be different from other hormones, resulting in several different waveforms that are representative of the particular oscillating pattern of the particular hormone. Depending on the particular hormone, those waveform patterns P may include gradually curved crests and troughs (e.g., similar to a sine wave, as shown in FIG. 2A), sharp or narrow crests and troughs (e.g., similar to a spike wave), angular crests and troughs (e.g., similar to a square wave, as shown in FIG. 2B), etc.

Figure 2A:
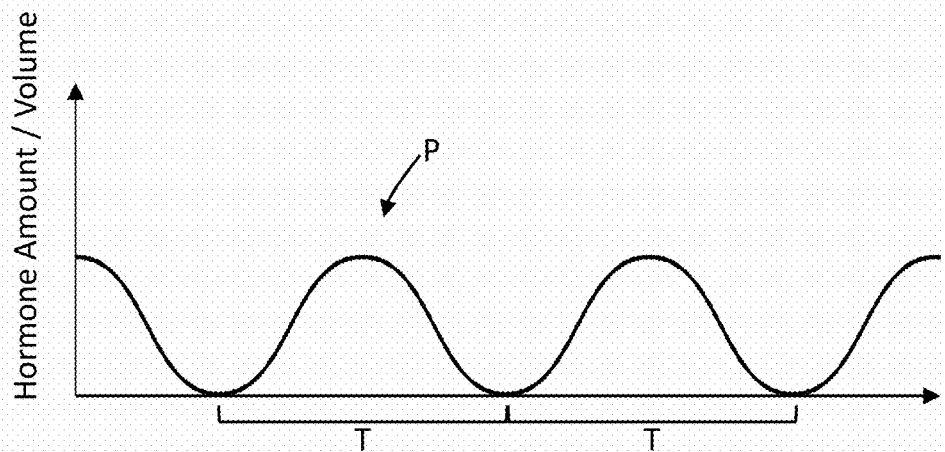
FIG. 2A is an exemplary waveform representing a target physiological cadence of a hormone in the human body, as described in accordance with at least one embodiment of the present invention.
Figure 2B:
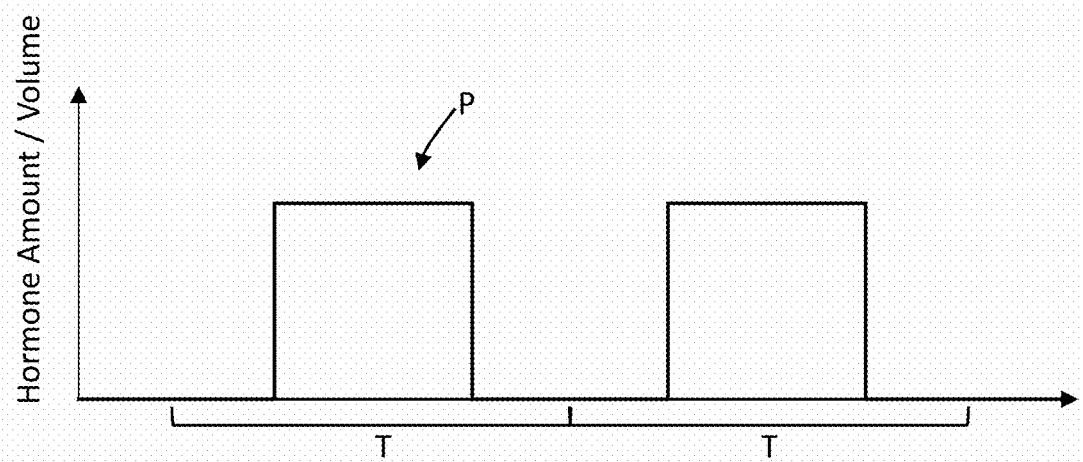
FIG. 2B is another exemplary waveform representing a target physiological cadence of a hormone in the human body, as described in accordance with at least one embodiment of the present invention.
Figure 3A:
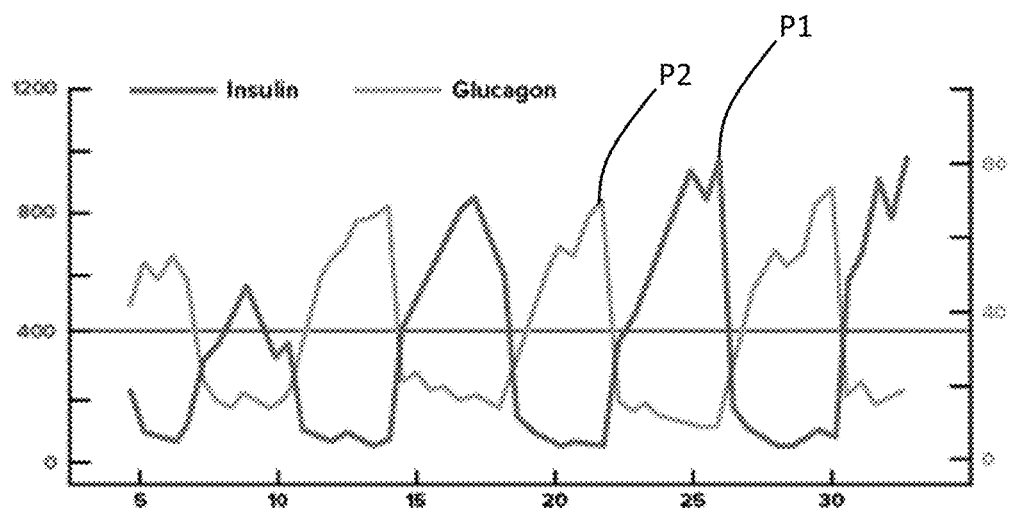
FIG. 3A is an exemplary diagram illustrating representative of a normal physiological cadence of two hormones (insulin and glucagon) measured over a period of time in minutes.

It should be noted that the waveforms illustrated in FIGS. 2A and 2B, for example, are shown for purposes of illustration in that the actual waveform or pulsatile secretion of a hormone in the human body is often not a perfect sine wave or square wave. Rather, FIG. 3A illustrates a more realistic waveform pattern P1 and/or P2 of target physiological cadences. For example, FIG. 3A is representative of a target physiological cadence of insulin (represented by P1) and a target physiological cadence of glucagon (represented by P2) of normal physiology measured over a period of time in minutes.

Furthermore, in some cases, the target physiological cadence, as used herein, is the ideal or desired cadence or pulsatile secretion of the particular hormone that the healthcare provider or subject would like to achieve. Since the physiological cadence of the same hormone can vary from person to person and can often depend on several demographic and other factors, such as, but not limited to, age, gender, weight, environmental factors, health, etc., determining the target physiological cadence of several embodiments of the present invention can, in many cases, include identifying a target or class of individuals by age, gender, weight, overall health, and other desired factors.

As just an example, the physiological cadence or secretion of oxytocin can vary significantly depending on the particular age and gender of the subject.

Moreover, with the hormone, and in some cases, the target class of individuals, defined or selected, determining or identifying the pulsatility or physiological cadence of the hormone may also include referencing a chart, look-up table, books, research papers, publications, or other reference material(s) previously prepared that identify a known pulsatility of particular hormones. The reference material(s) may, in some cases, include separate entries or itemized records for different demographics or classes of individuals, for example, identifying a different target physiological cadence of oxytocin for a thirteen year-old girl as compared to a thirty-five year-old woman.

In any case, the reference material(s) and data contained therein is/are based on known information as a result of extensive research, testing, peer reviews, etc. As just an example, the pulsatile release or secretion of insulin is known to be every four to eight minutes (4-8 min), and in some cases, every five to six minutes (5-6 min), resulting in a generally curve-shaped waveform pattern P and/or P1 with a wavelength that is completed in time T of approximately 4-8 minutes. In this manner, the exemplary waveform patterns P shown in FIG. 2A and/or P1 shown in FIG. 3A, with time T of 4-8 minutes may be selected as a target physiological cadence of the hormone insulin.

Referring again to FIG. 1A, the method 100 of at least one embodiment also includes creating a subject profile, generally referenced as 106. The subject profile includes storable data about the subject or patient, which may in some cases include, but is in no way limited to, the subject's demographic information or physical reports such as age, sex, weight, etc., the patient's medical history, etc.

Furthermore, the subject profile of at least one embodiment of the present invention includes a diagnosis or determination of the subject's physiological secretion of the selected or identified hormone. More specifically, the subject profile includes a pre-treatment identification or diagnosis (e.g., by the healthcare provider through laboratory testing, diagnostics, and/or a detailed patient medical history or other history) that relates to or otherwise defines or estimates the subject's secretion pattern (if any) of the identified hormone or the hormone level(s) or amount(s) in the subject.

The hormone secretion diagnosis portion of the subject profile can be defined or estimated by the healthcare provider through a review of test results (e.g., blood tests), a review of medical examination results (e.g., medical imaging examinations), and/or through physical examinations (e.g., observation, blood pressure tests, etc.) In some cases, the hormone secretion diagnosis can be made or estimated based solely on questions and answers and physical observation of the subject.

Figure 3B:
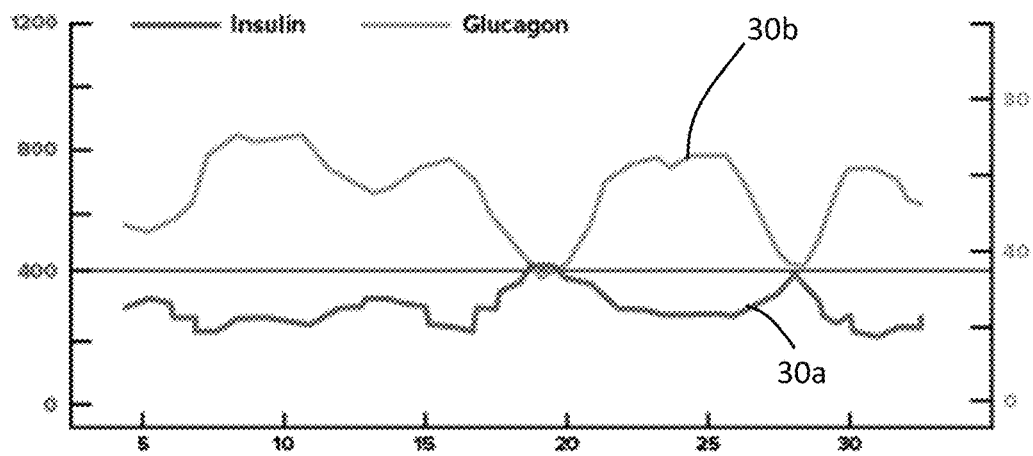
FIG. 3B is an exemplary diagram representative of an abnormal physiological cadence of two hormones (insulin and glucagon) measure over a period of time in minutes.

FIG. 3B illustrates an exemplary waveform of the subject's pre-treatment or abnormal secretion 30a, 30b of one or more hormones. More specifically, FIG. 3B shows an exemplary pre-treatment secretion of insulin (represented at 30a) and glucagon (represented at 30b), shown abnormal physiology for which treatment is desired. Of course, other hormones (in addition to insulin and glucagon) can be represented through similar or different pretreatment waveforms and are within the full spirit and scope of the various embodiments of the present invention.

For instance, as an example, an 11-year-old subject who exhibits physical evidence of early onset of puberty, can be diagnosed by the healthcare provider with a high level of gonadotropin or other puberty-related hormones. This diagnosis can be made, in several instances, by observation alone and without the need for additional physical or medical exams or blood tests. Alternatively, diagnosis of high or low levels of other hormones, or abnormal secretion rates of a particular hormone may need, require or benefit from one or more exams, tests or further observations.

Referring again to FIG. 1A, the method 100 of at least one embodiment also includes developing a dosing model, referenced as 108, that in some cases may be at least partially based on at least one or both of: (a) the target physiological cadence of the hormone and (b) the subject profile. In particular, as provided herein, the dosing model of at least one embodiment of the present invention identifies or otherwise includes an identification of the hormone to be used or delivered to the subject (e.g., the hormone previously identified in 102), and at least one, although in most cases a plurality of bolus delivery specifications, such as pressure, frequency, volume, concentrations, oscillation, etc.

More specifically, a bolus, as used herein, is a single dose of a medical substance and/or drug given all at once. In at least one embodiment, each bolus or each intravenous exogenous bolus introduction or delivery includes an amount or volume of the hormone (e.g., the hormone previously identified in 102), which is often, but not necessarily always, combined with a delivery medium which may include, but is in no way limited to saline, water, sterile water, etc.

Next, as shown at 110, the dosing model is executed through or by a plurality of precise, controlled and in some cases dynamic intravenous exogenous bolus introductions of the hormone according to the bolus delivery specifications identified in the dosing plan.

In other embodiments, the dosing model may be executed through or by a plurality of precise, controlled, and in some cases, dynamic endogenous bolus introductions of the hormone according to the bolus delivery specifications. For example, an implantable device may be fully or partially implanted or inserted into the subject's body. The implantable device being capable of endogenously releasing the hormone(s) according to the dosing model and the bolus delivery specifications thereof. The implantable device may be pre-programmed (e.g., prior to implantation) and/or programmed while implanted, for example, through a separate device or computer that is communicative therewith wirelessly or through a wired connection.

Figure 3C:
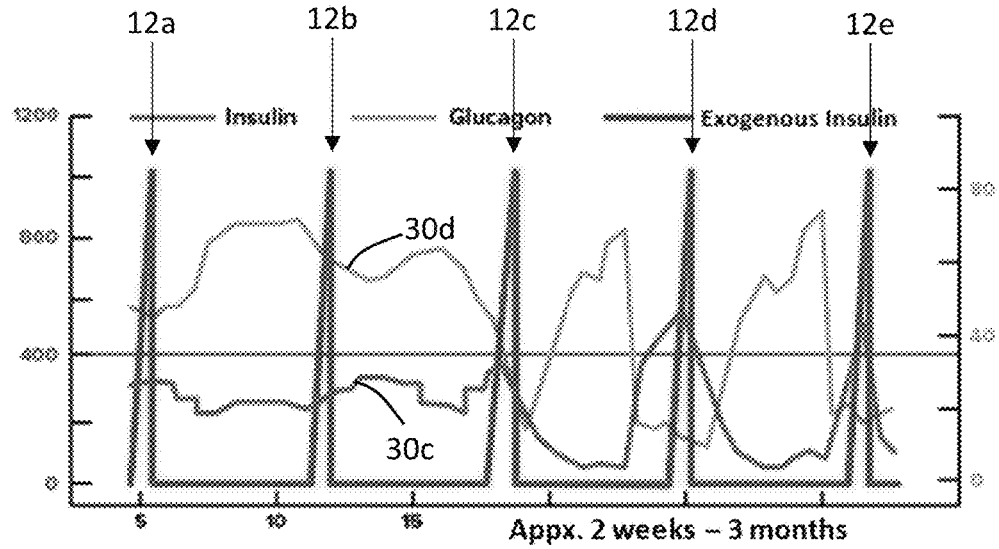
FIG. 3C is an exemplary diagram illustrating controlled intravenous delivery of at least one hormone according and its impact on the abnormal cadence illustrated in FIG. 3B.

More specifically, in at least one embodiment, a desired goal is to mimic or replicate the previously identified target physiological cadence of the hormone P, P1, P2 and so on, as closely as possible. In some embodiments, this is accomplished through precise and controlled bolus introductions of the hormone into the subject, e.g., to approximate or mimic the normal physiologic secretion pathways of the particular hormone. FIG. 3C illustrates an exemplary series of bolus introductions 12a-12a-e, overlaid upon an at least partially corrected waveform or cadence of hormones 30c, 30d of a subject. More specifically, over time (e.g., after several sessions over a period of weeks or months), the subject's secretion pattern 30c, 30d of the particular hormone, e.g., insulin and glucagon, will begin to more closely mimic the target cadence P1, P2 (as shown in FIG. 3A) and as compared to the pre-treatment cadences 30a, 30 (as shown in FIG. 3B).

For example, using an intravenous access connected to a precision intravenous infusion pump that can be programmed to include one or more of the bolus delivery specifications (e.g., pressure, frequency, volume, concentration, etc.), the hormone can be dynamically delivered to mimic or closely resemble the target physiological cadence of the hormone. The bolus delivery specifications or infusion specification are selected based on the particular target oscillation pattern P (e.g., as shown in FIG. 2A-2B) or P1, P2 (e.g., as shown in FIG. 3A), and in some cases, the subject profile, including the subject's resistance to the hormone, the subject's diagnosis of the pre-treatment secretion pattern, and other physical and medical factors.

Particularly, the bolus specification(s) are selected and defined in a manner to achieve a desired waveform, for example, as exhibited by the oscillating pattern P, P1, P2 of the target physiological cadence.

Figure 4:
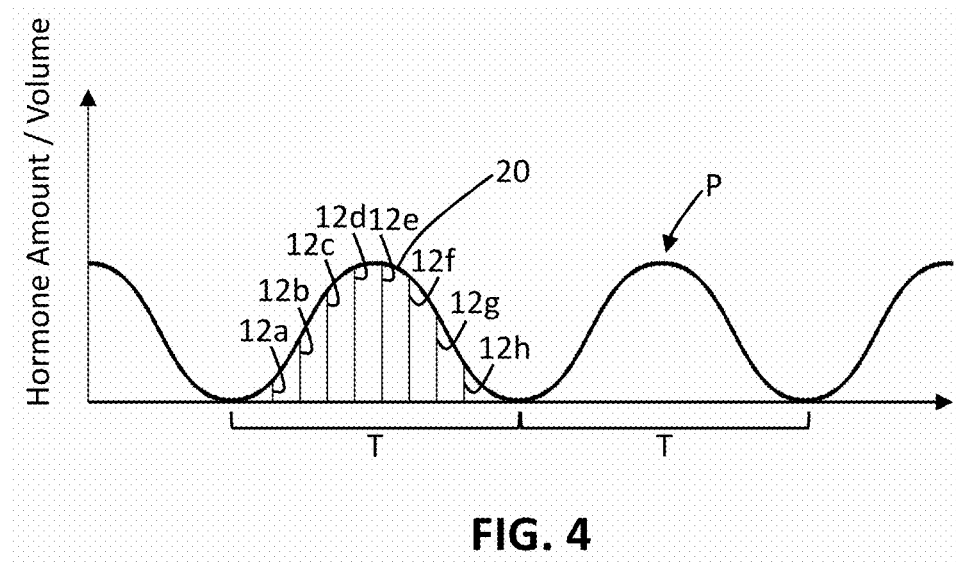
FIG. 4 is an exemplary waveform illustrating a plurality of dynamic and successive intravenous bolus introductions, as described in accordance with at least one embodiment of the present invention.

Accordingly, one solution, as provided in accordance with at least one embodiment of the present invention, is to introduce a plurality of successive and separate boluses (represented as 12a-h in FIG. 4) within the time T (defining the frequency), each of the separate and successive boluses having a particular defined or selected pressure, frequency, concentration, and/or volume (e.g., as represented by the height or volume axis in FIG. 4). In this manner, the dynamic bolus introductions, e.g., within time T, can be used to more closely mimic or resemble the target oscillation pattern P. The boluses are referred as dynamic in this example because at least one of the bolus specifications (e.g., volume, pressure, frequency, concentration) can be different between at least some of the boluses within a single amount of time T.

For example, still referring to FIG. 4, boluses 12a-12h define a continuous or constant frequency (e.g., as shown via the constant spacing of the boluses 12a-12h along time T; however, bolus 12a has a lower volume of the hormone or hormone solution and/or a lower pressure than the next bolus 12b. Similarly, bolus 12b has a lower volume of the hormone or hormone solution and/or a lower pressure than the next bolus 12c. The dynamic changing of the volume or pressure in this example causes the resultant bolus waveform 20 to closely mimic or resemble the target waveform pattern P.

It should be noted that in addition to or instead of the varying or dynamic pressure or volume, the frequency of the boluses may change throughout the execution of the dosing model in order to achieve a dosing waveform that mimics or closely resembles the target waveform pattern P.

Accordingly, the intravenous infusion pump as used in connection with certain embodiment of the present invention may be programmed in a manner such that the particularly desired frequency of boluses (e.g., the number of successive bolus introductions to be delivered within time T), the volume of each separate bolus (e.g., the amount of hormone or hormone solution in each bolus), and, in some cases, the pressure of each bolus may be programmed into the intravenous infusion pump such that the execution of the dosing model is accomplished through the dynamic introduction of successive boluses to achieve the desired wavelength pattern that resembles the target pattern P.

It should also be noted that other embodiments or implementations may use an infusion pump that is capable of varying one or more of the bolus specifications during a single bolus. For example, the pump may be configurable or programmable to dynamically change the pressure and/or volume in or otherwise throughout a single bolus. In other words, in order to achieve the target oscillation pattern P, shown in FIG. 2A for example, the pressure or volume of a single, continuous bolus may, in such an embodiment, begin low, then gradually increase until the bolus or time T reaches the crest or peak of the waveform, then gradually decrease to form the curved waveform pattern. Of course, in order to achieve other target waveform patterns, the pump may be configured or programmed in a manner to correspondingly dynamically change one or more of the bolus specifications.

Figure 5:
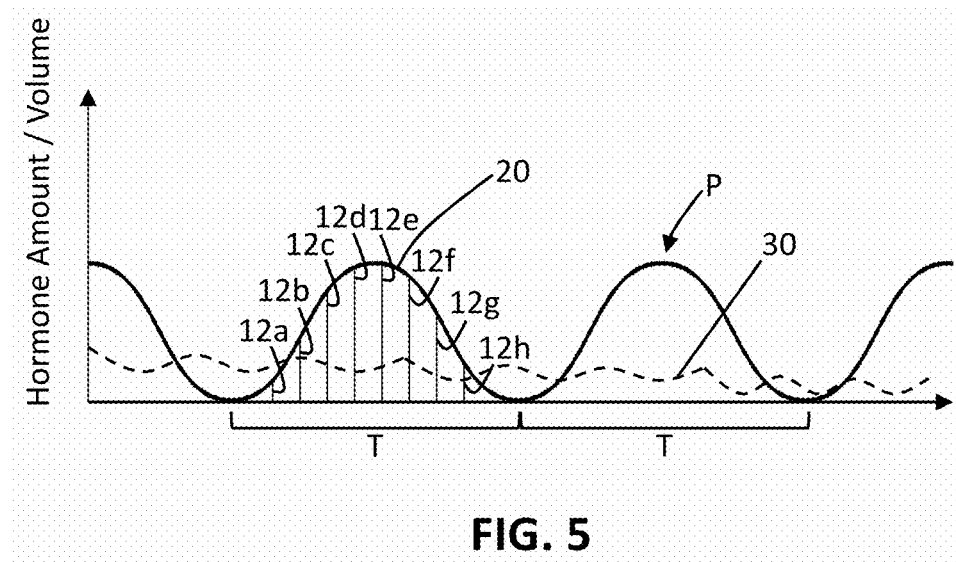
FIG. 5 is another exemplary waveform illustrating a plurality of dynamic and successive intravenous bolus introductions combined with a subject's pre-treatment hormone cadence, as described in accordance with at least one embodiment of the present invention.

FIG. 5 is an exemplary illustrating showing the subject's pre-treatment (abnormal) secretion pattern 30 overlaid upon the several dynamic boluses of the hormone, used to mimic or approximate the normal physiologic hormone signaling pathways.

In some cases, the one or more bolus delivery specifications are selected to generate a bolus delivery waveform that, when combined with or when taking into consideration the subject's pre-treatment secretion pattern 30, at least partially resembles the target physiologic cadence or pattern P of the hormone. More specifically, as provided herein, in at least one embodiment, the healthcare provider may define or estimate (e.g., based on clinical tests or exams, observation, etc.) a pre-treatment cadence or hormonal level, generally represented as 30. The pre-treatment cadence or hormonal level 30 may be taken into consideration when defining the bolus specifications (e.g., concentration, volume, frequency, pressure, etc.) for the intravenous delivery of the hormone.

For example, the subject's hormone secretion level or pattern 30 may not be zero or non-existent, meaning that in some cases, the subject may be secreting some of the hormone, albeit not in a desired or target cadence. In such a case, the measured or estimated hormonal level or pattern 30 of the subject may be considered such that when introducing the bolus(es) in accordance with at least one embodiment of the present invention, the delivery specification(s) (e.g., frequency, volume, pressure) may be selected such that when the hormones are introduced to the subject's body through the bolus(es), they more closely mimic or resemble the target oscillation pattern P, as generally exemplified in FIG. 5.

Referring now to FIG. 1B, the method 100 of at least one embodiment also includes sensing the subject's physiological response to an at least partial execution of the dosing model, as generally shown at 112. More specifically, throughout the execution of the dosing model and/or after execution of the dosing model, in some embodiments, the subject is analyzed (e.g., through observation, one or more medical examinations, one or more medical or physical tests, etc.) in order to determine or diagnose the subject's response to the dosing model. The particular examination(s), test(s), and/or observation may be highly dependent on the particular hormone being introduced through the dosing model, the particular or overall health of the subject, and other considerations or factors. For instance, sensing or testing the subject's physiological response to the dosing model may, in some cases, include one or more medical examination or sensing equipment, or in other cases, physical observation of the subject. Moreover, a feedback loop or feedback mechanism may be implemented or employed whereby the outcome, goal or expected change in a target cell os measured by the subject's physiologic response to the treatment or dosing model.

In some embodiments, the dosing model may be adjusted or changed based at least in part on the observation or examination of the subject, to create a modified dosing model, as shown at 114 in FIG. 1B. As just an example, the modified dosing model may include modified dosing specification, such as modified bolus frequencies, volumes or pressures, modified time or interval T within which to introduce the bolus(es), etc.

In any event, with the modified dosing model defined, as shown at 116 in FIG. 1B, the modified dosing model will be executed, in much the same manner as the initial dosing model, but with modified specifications.

The process of observation/examination, followed by modification of the dosing model and execution of the modified dosing model can repeat, as necessary or as diagnosed by the healthcare provider.

It is also contemplated and within the full spirit and scope of certain embodiments of the present invention that the system and method disclosed herein can be used to provide similar hormone bolus introductions, or other introductions, treatments or perfusions to a human organ that has been fully removed from the human body, for example, an organ that may otherwise be discarded, in an attempt to rejuvenate the organ so that is can be effectively and subsequently re-introduced in to a human body. More specifically, the method and/or system of at least one embodiment can provide bolus introductions of one or more hormone (for example, but in no way limited to insulin) to a human organ, gland, etc. (for example, but in no way limited to a kidney) that has been fully removed from the human body in an attempt to rejuvenate the organ, gland, etc.

In some cases, the bolus introductions of the hormone into the extracted or removed human organ are successive and dynamic in a similar manner as described in accordance with other embodiments disclosed herein in that the bolus specifications may be selected in a manner to mimic or closely resemble a target physiologic cadence of the hormone, for example, in a healthy subject. It should also be noted that with the organ removed from the human body, there is a lower concern, or in some cases no concern, of over stimulating the body with the hormone during the treatments.

For example, using a three-day-old human kidney that was extracted or otherwise removed from the human body, after a control period, the kidney was augmented with a periodic infusion of insulin for approximately two hours at a concentration similar to the amount of insulin projected to be seen by a kidney in situ in a person who would receive physiological insulin resensitization (PIR) treatment.

The perfusate was sampled before and after passing through the kidney at five to fifteen minute intervals to determine if glucose was being removed and to determine any changes in electrolytes, such as sodium and potassium. The kidney was able to ingest levels of glucose from the perfusate well in excess of the control level, and better alter the electrolyte concentrations in a manner similar to a kidney in situ.

The ability of the kidney to generate and excrete urine was monitored via a catheter attached to a ureter. The kidney did not excrete during the control period, but after about one hour of treatment (i.e., bolus introductions of insulin similar to PIR treatment), the kidney began to excrete urine.

Two millimeter punch biopsies were examined approximately every fifteen minutes with a specialized Acquyre Biosciences microscope that produces pseudocolored images at a cellular level that reflect the extent of intracellular organellar movement. Intracellular movement is dependent on the availability of cytoplasmic ATP (adenosine triphosphate). After approximately thirty minutes of the perfusion similar to PIR treatment, there was an obvious increase in intracellular movement relative to the control period. This result is consistent with an increase in intracellular ATP in response to the treatment.

Additional experiments will determine kidney viability when control perfusions are compared to perfusions augmented with insulin treatments and perfusions that are similar to PIR treatments, including the same amount of insulin delivered continuously rather than periodically. A host of parameters will be assessed, including transcriptional patterns, phosphorylation, and kidney function. Variables such as the amount of insulin (or other hormone) for optimal recovery will be determined and help guide subsequent experiments with human kidneys and other organs.

Figure 6:
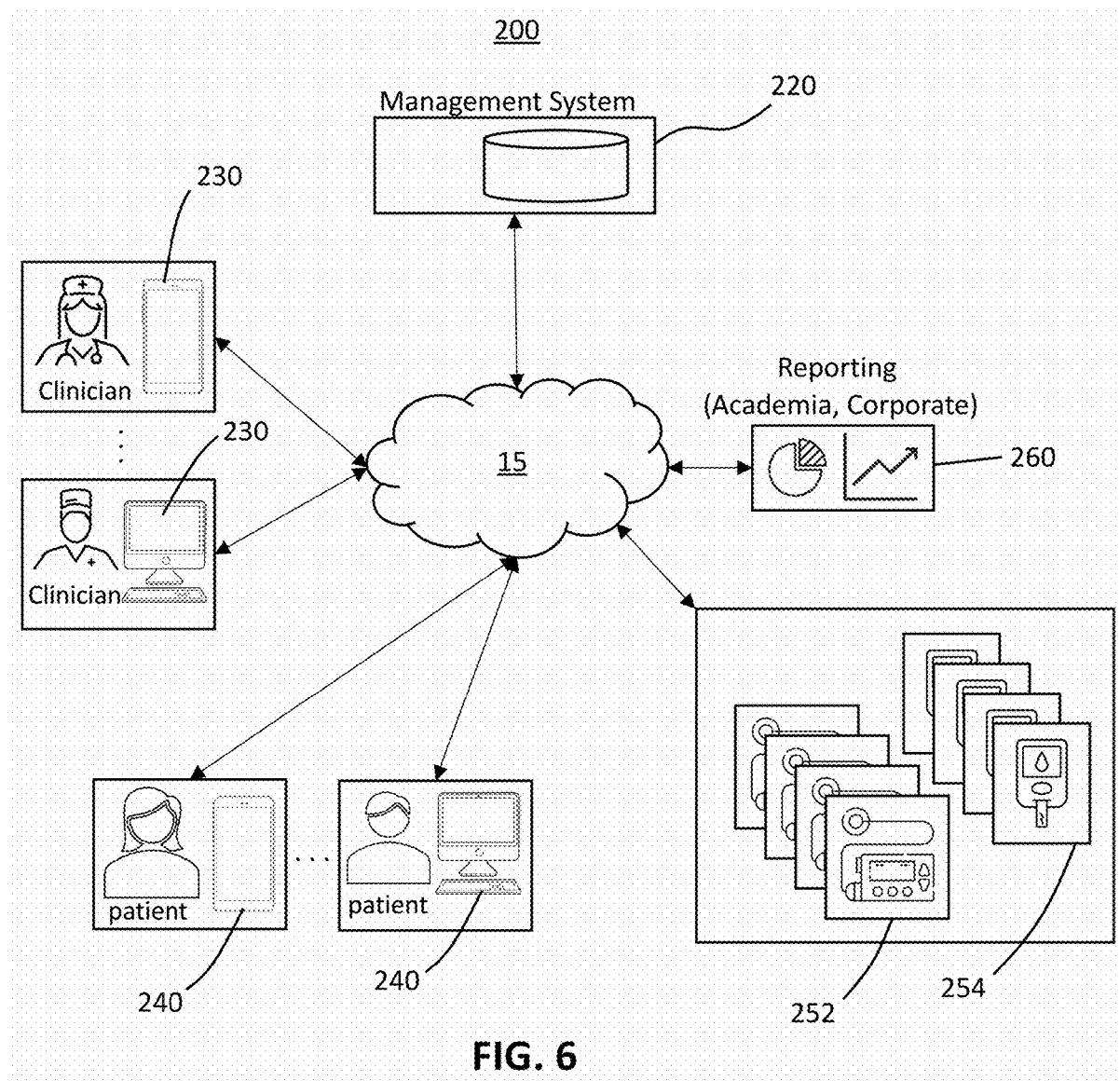
FIG. 6 is a schematic block diagram of a system, and several communicative components of the system, as disclosed in accordance with at least one embodiment of the present invention.

Furthermore, referring now to FIG. 6, a block network diagram illustrating the system 200 as disclosed in accordance with at least one embodiment, as well as some of the components that may be used to implement the methods 100 as described herein is shown.

For instance, in at least one embodiment, the system 200 includes at least one global-based or remote management system, generally referenced as 220, disposed in a communicative relation with a plurality of user devices (e.g., a clinician or medical personnel device 230, a patient device 240, one or more connected medical devices 252, 254, one or more reporting entities or devices 260, etc.) for example, via a network 215.

The network 215, as used herein, may include virtually any computer, communication or data network such as the World Wide Web, Internet, Intranet, local area network (LAN), Wide Area Network(s), metro area network (MAN), Telecommunication Network(s) (e.g., 3G, 4G, 5G, LTE), cellular or wired networks, similar networks and any combination(s) thereof, etc.

Moreover, the management system 220, as disclosed in connection with certain embodiments of the present invention is structured and/or configured to manage, store and process account or patient information (e.g., usernames, passwords, account information, contacts, etc.), facilitate the storage and analysis of patient data, patient test results, clinical or other information (e.g., as provided by the clinical or medical personnel device(s) 230, the patient device(S) 240, one or more of the connected device(s) 252, 254, etc.), facilitate data mining and reporting, etc., as described herein.

In this manner, the management system 220 of at least one embodiment of the present invention may include at least one web or cloud-based computer or server, desktop computer, laptop computer, tablet, mobile or handheld computer, etc. capable of facilitating implementation of the present invention disclosed herein. The management system 220 may include one or more databases or other like storage components, implemented in hardware and/or software to store data and facilitate implementation of at least one embodiment of the present invention in the intended manner.

Furthermore, the user devices, for example, the clinician or medical personnel device(s) 230 and/or the patient device (S) 240, may include virtually any computer-based device communicative with the management system 220 and configured to or capable of implementing various aspects of the present invention as described herein. For example, in at least one embodiment, a clinician or medical personnel may utilize the corresponding device 230 to access certain information, data, reports, processes, etc. managed or processed by the management system 220 via a clinician or medical personnel interface. Similarly, in at least one embodiment, a patient may utilize the corresponding device 240 to access certain information, data, reports, processes, etc. managed or processed by the management system 220 via a patient interface. In many instances, some data, information, reports, test results, medical records, etc. accessible by the medical personnel interface are not accessible by the patient interfaces, and some data, information, reports, test results, medical records, etc. accessible by the patient interface are not accessible by the medical personnel interface.

In any event, the user devices 230, 240 may include, but are not limited to, mobile devices or mobile terminals such as, for example, mobile phones, smartphones, tablet computers, wearable devices, etc., as well as laptop or mobile computers, desktop computers, video game consoles, mobile video game devices, etc. Accordingly, in some embodiments or implementations, the user or mobile device(s) 30 may include, for example, an APPLE® iPHONE®, APPLE® iPAD®, ANDROID® based phone or tablet, etc.

Furthermore, the connected medical devices, represented schematically as 252 and 254 in FIG. 6, of at least one embodiment may include virtually any medical texting equipment, medical procedure equipment, or other medical equipment that may be used to implement various embodiments of the present invention, such as, but in no way limited to one or more pumps 252 (e.g., infusion pumps), monitors or texting equipment (e.g., blood glucose monitors 254), blood pressure monitors, heart or cardiac-monitoring devices, telemetry monitoring devices, etc.

Accordingly, the various embodiments of the global or remote management system 220, the user devices 230, 240 and the connected medical devices 252, 252 of at least one embodiment each includes at least one or all of the following components, among other components and devices structured to facilitate implementation of the present invention in the intended manner: a computer processor or processing circuitry, memory, one or more data storage devices, and one or more communication or network device(s) or interface(s). For each of the devices, the corresponding processor or processing circuitry may be coupled to the corresponding memory, storage device and network interface to facilitate implementation of the present invention in the intended manner.

Specifically, as used herein, for each device, the processor or processing circuitry of at least one embodiment may be realized as one or more hardware logic components or circuits, such as, without limitation, one or more types of components that may include field programmable gate arrays (FPGAs), application specific integrated circuits (ASICs), application specific standard products (ASSPs), system-on-a-chip systems (SOCs), general purpose microprocessors, microcontrollers, digital signal processors (DSPs), or other like hardware components that can execute or implement computer instructions, software, etc., including, for example, the various features and components as described in accordance with at least one embodiment of the present invention and configured to implement or facilitate the implementation of the method 100 herein.

Further, for each device, the memory device, as used herein, may include but is not limited to volatile or non-volatile memory, such as random access memory (RAM), read-only memory (ROM, flash memory, etc., or other like device(s) configured to implement the present invention in the intended manner, for example, by storing and assisting with the execution of one or more applications, modules, or components capable of implementing the system 200 and method 100 described herein. It should be noted that non-transitory computer readable media includes all computer-readable media except for a transitory, propagating signal.

The data storage device(s), as used herein, may include a magnetic storage, optical storage, or other types of storage and may be realized as a hard disk drive, CD/DVD, USB drive, solid state drive, virtual drive, could-based storage drive, or other types of volatile or non-volatile memory.

In some embodiments, the memory and/or storage device is configured to store software. Software shall be construed broadly to mean any type of instructions, whether referred to as software, firmware, middleware, microcode, hardware description language, or otherwise. Instructions may include code, e.g., source code, binary code, executable code or other format. The instructions or software, when executed by the processor or processing circuitry, cause the processing circuitry to perform various processes, methods or steps described herein.

Moreover, the communication device(s), as used herein, may include a network communication hardware/software component structured to facilitate communication between the management platform/system 220 of the present invention and the various devices 230, 240.

More specifically, the management system 220 of at least one embodiment of the present invention is capable of receiving various information and data, such as text results, patient monitoring, etc. from the various devices 230, 240, 252, 254 in connection with the method(s) 100 described herein. Such information can include, but is not limited to, the detected hormone(s), (e.g., as provided at 102), the target physiological cadence of the hormone (e.g., as provided at 104), the subject or patient profile (e.g., as provided at 106), the dosing model (e.g., as provided at 108), the patient's physiologic response to the dosing model (e.g., as provided at 112), etc.

Figure 7:
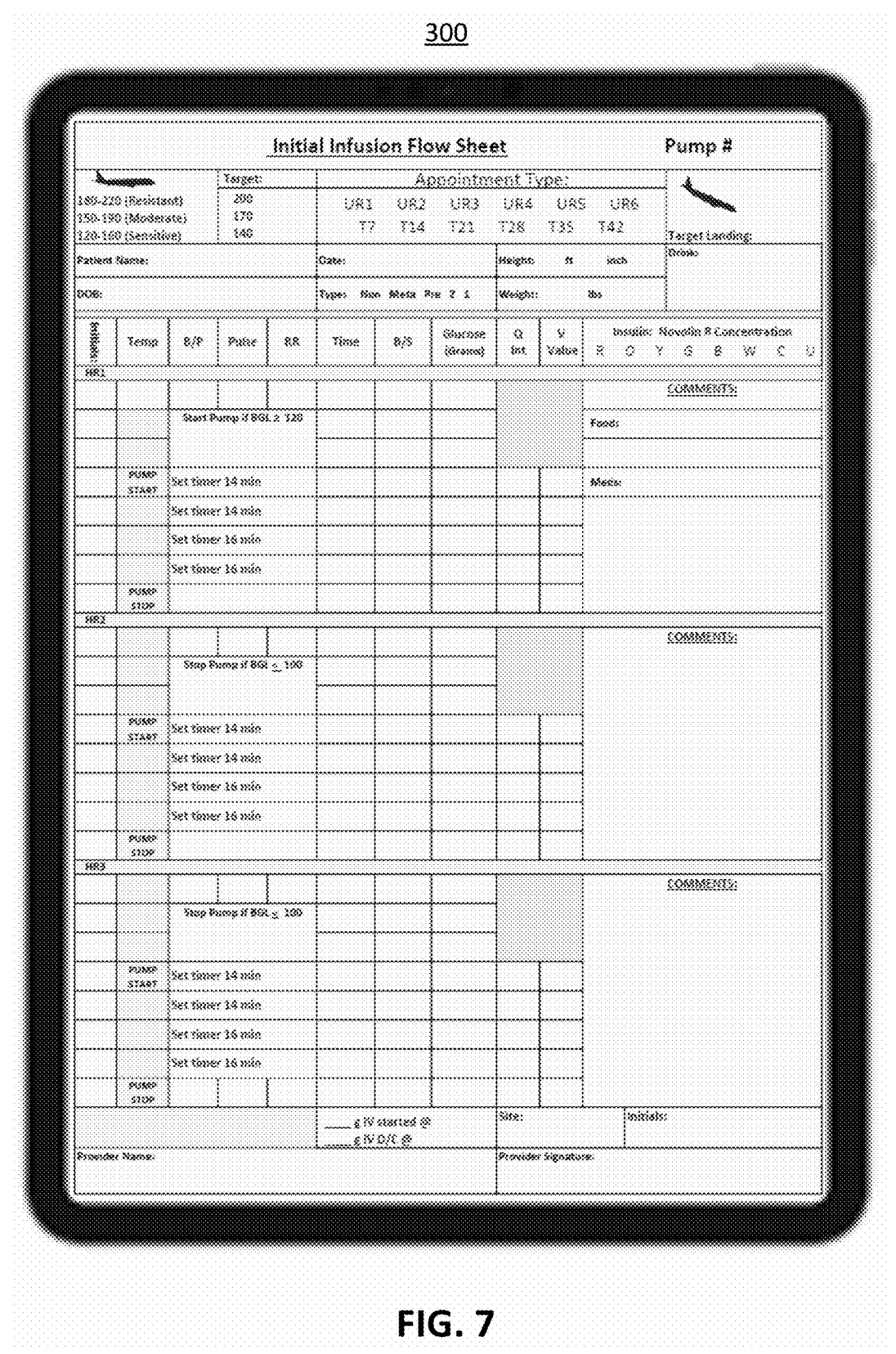

FIG. 7 illustrates an exemplary infusion flow sheet that tracks the infusions provided to each patient. The infusion flow sheet 300 may be implemented in software and filled out or managed by the clinician device 230 and/or patient device 240 of at least one embodiment of the present invention. This sheet provides important tracking information for each infusion and for each patient, which can be used by the physician and/or the management system 220 to predict outcomes, adjust care plans or dosing models, and/or otherwise track the patient's progress of infusions and treatment.

In some cases, the management system 220 is equipped with, has access to, or is able to obtain various research data, publicly available information, or other knowledge base such that (with the exception to patient-specific data, such as the patient profile, patient's test results, monitoring data, etc.) the management system 220 may already have access to some of the data or information, such as the target physiologic cadence, as used herein.

In this manner, the management system 220 of at least one embodiment is capable of or structured to receive and/or process the various information or data described herein and provided one or more recommendations, e.g., medical recommendations based at least in part thereupon to the medical personnel (e.g., physician, clinician, nurse, etc.). Using the recommendations provided by the management system 220, the medical personnel can then execute medical decisions (e.g., by initiating tests, developing a dosing model, modifying the dosing model, executing the dosing model or modified dosing model, etc.) In some cases, it is also contemplated that the management system 220 of at least one embodiment is capable of and configured to make decisions or implement procedures (e.g., by initiating tests, developing a dosing model, modifying the dosing model, executing the dosing model or modified dosing model, etc.) without intervention by the medical personnel or clinician.

It should be noted that, in some cases, the management system 220 of at least one embodiment may include, use or implement machine learning, large language model(s) (LLM) and/or other types of artificial intelligence (AI) systems, whether integral with the system 220 or external to the system 220, to predict outcomes, determine which hormone(s) to inject, determine the dosing model, determine what changes, if any need to be made to the dosing model, etc.

Since other modifications and changes varied to fit particular operating requirements and environments will be apparent to those skilled in the art, the invention is not considered limited to the example chosen for purposes of disclosure, and covers all changes and modifications that do not constitute departures from the true spirit and scope of this invention. This written description provides an illustrative explanation and/or account of the present invention. It may be possible to deliver equivalent benefits using variations of the specific embodiments, without departing from the inventive concept. This description and these drawings, therefore, are to be regarded as illustrative and not restrictive.

The invention claimed is:

1. A method for tuning hormone receptors in a subject, the method comprising:
   identifying a hormone which will bind to the hormone receptors,
   determining a target physiologic cadence of the hormone,
   creating a subject profile for the subject, the subject profile comprising a hormone secretion diagnosis relating to a pre-treatment secretion pattern of the hormone in the subject,
   and
   executing a dosing model through a plurality of successive and dynamic bolus introductions of the hormone according to a plurality of bolus delivery specifications, the dosing model being at least partially based on (a) the target physiologic cadence of the hormone and (b) the subject profile, wherein the dosing model comprises an identification of the hormone and the plurality of bolus delivery specifications.

2. The method as recited in claim 1 wherein the plurality of bolus delivery specifications comprises a pressure, a frequency and a volume associated with each of the plurality of successive and dynamic bolus introductions.

3. The method as recited in claim 2 wherein the plurality of bolus delivery specifications are selected to generate a bolus delivery waveform that at least partially resembles the target physiologic cadence of the hormone.

4. The method as recited in claim 2 wherein the plurality of bolus delivery specifications are selected to generate a bolus delivery waveform that, when combined with the pre-treatment secretion pattern of the hormone in the subject, at least partially resembles the target physiologic cadence of the hormone.

5. The method as recited in claim 2 wherein the plurality of bolus delivery specifications are selected to generate a bolus delivery waveform, wherein at least one of the plurality of bolus delivery specifications is changed within a single wavelength of the bolus delivery waveform.

6. The method as recited in claim 5 wherein, within the single wavelength, the volume of at least one of the plurality of successive and dynamic bolus introductions is different from the volume of at least another one of the plurality of successive and dynamic bolus introductions.

7. The method as recited in claim 5 wherein, within the single wavelength, the pressure of at least one of the plurality of successive and dynamic bolus introductions is different from the pressure of at least another one of the plurality of successive and dynamic bolus introductions.

8. The method as recited in claim 2 further comprising using a pump to intravenously deliver the plurality of successive and dynamic bolus introductions to the subject, the pump being configured to operate with the plurality of bolus delivery specifications.

9. The method as recited in claim 1 wherein the plurality of successive and dynamic bolus introductions are intravenous exogenous bolus introductions.

10. The method as recited in claim 1 wherein the plurality of successive and dynamic bolus introductions are endogenous bolus introductions.

11. The method as recited in claim 1 further comprising sensing a physiologic response of the subject to an at least partial execution of the dosing model.

12. The method as recited in claim 11 further comprising adjusting the dosing model to create a modified dosing model based at least upon the detected physiologic response of the subject, and executing the modified dosing model through a plurality of bolus introductions of the hormone.

13. A method for tuning hormone receptors in a subject, wherein a hormone binds to the hormone receptor, the method comprising:
  determining a target physiologic cadence of the hormone,
  developing a dosing model, the dosing model being at least partially based on the target physiologic cadence of the hormone, wherein the dosing model comprises an identification of the hormone and a plurality of bolus delivery specifications, the plurality of bolus delivery specifications comprising a pressure, a frequency and a volume,
  selecting the plurality of bolus delivery specifications that will generate a bolus delivery waveform that at least partially resembles the target physiologic cadence of the hormone, wherein at least one of the plurality of bolus delivery specifications is changed within a single wavelength of the bolus delivery waveform, and
  executing the dosing model through a plurality of successive and dynamic bolus introductions of the hormone according to the plurality of bolus delivery specifications.

14. The method as recited in claim 13 further comprising creating a subject profile, the subject profile comprising a hormone secretion diagnosis relating to a pre-treatment secretion pattern of the hormone in the subject.

15. The method as recited in claim 14 wherein the dosing model is at least partially based on the subject profile.

16. The method as recited in claim 13 wherein, within the single wavelength, the volume of at least one of the plurality of successive and dynamic bolus introductions is different from the volume of at least another one of the plurality of successive and dynamic bolus introductions.

17. The method as recited in claim 13 wherein, within the single wavelength, the pressure of at least one of the plurality of successive and dynamic bolus introductions is different from the pressure of at least another one of the plurality of successive and dynamic bolus introductions.

18. The method as recited in claim 13 further comprising using a pump to intravenously deliver the plurality of successive and dynamic bolus introductions to the subject, the pump being configured to operate with the plurality of bolus delivery specifications.

19. The method as recited in claim 18 further comprising adjusting the dosing model to create a modified dosing model based at least upon the detected physiologic response of the subject, and executing the modified dosing model through a plurality of intravenous exogenous bolus introductions of the hormone.

20. The method as recited in claim 13 further comprising sensing a physiologic response of the subject to an at least partial execution of the dosing model.

* * * * *